United States Patent
Suzuki

(10) Patent No.: US 10,478,385 B2
(45) Date of Patent: Nov. 19, 2019

(54) DENTAL ADHESIVE MATERIAL KIT

(71) Applicant: KURARAY NORITAKE DENTAL INC., Kurashiki-shi (JP)

(72) Inventor: Kenji Suzuki, Tainai (JP)

(73) Assignee: KURARAY NORITAKE DENTAL INC., Kurashiki-shi (JP)

(*) Notice: Subject to any disclaimer, the term of this patent is extended or adjusted under 35 U.S.C. 154(b) by 0 days.

(21) Appl. No.: 16/062,667

(22) PCT Filed: Dec. 12, 2016

(86) PCT No.: PCT/JP2016/005108
§ 371 (c)(1),
(2) Date: Jun. 15, 2018

(87) PCT Pub. No.: WO2017/104128
PCT Pub. Date: Jun. 22, 2017

(65) Prior Publication Data
US 2019/0000722 A1  Jan. 3, 2019

(30) Foreign Application Priority Data
Dec. 18, 2015 (JP) .................. 2015-247828

(51) Int. Cl.
| | | |
|---|---|---|
| *C08F 2/46* | (2006.01) |
| *C08F 2/50* | (2006.01) |
| *C08G 61/04* | (2006.01) |
| *A61K 6/083* | (2006.01) |
| *A61K 6/00* | (2006.01) |
| *A61K 6/04* | (2006.01) |

(52) U.S. Cl.
CPC ............... *A61K 6/083* (2013.01); *A61K 6/00* (2013.01); *A61K 6/0023* (2013.01); *A61K 6/0052* (2013.01); *A61K 6/04* (2013.01)

(58) Field of Classification Search
CPC ........ A61K 6/083; A61K 6/04; A61K 6/0052; A61K 6/00; C08F 2/46; C08F 2/50
USPC ............ 522/38, 7, 6, 71, 189, 184, 1; 520/1
See application file for complete search history.

(56) References Cited

U.S. PATENT DOCUMENTS

| | | |
|---|---|---|
| 5,908,879 A | 6/1999 | Kawashima et al. |
| 2005/0009946 A1 | 1/2005 | Oguri et al. |
| 2010/0130682 A1 | 5/2010 | Hinamoto et al. |
| 2016/0038382 A1 | 2/2016 | Kawashima et al. |

FOREIGN PATENT DOCUMENTS

| | | | |
|---|---|---|---|
| JP | 2-258602 A | | 10/1990 |
| JP | 10-036116 A | | 2/1998 |
| JP | 2005-239560 | * | 9/2005 |
| JP | 2005-239560 A | | 9/2005 |
| JP | 2009-167132 A | | 7/2009 |
| JP | 2011-225526 A | | 11/2011 |
| JP | 2014-114245 A | | 6/2014 |
| JP | 2014-227370 A | | 12/2014 |
| JP | 2014-231493 A | | 12/2014 |
| WO | WO 2008/087977 A1 | | 7/2008 |
| WO | WO 2013/046648 A1 | | 4/2013 |
| WO | WO 2014/156138 A1 | | 10/2014 |

OTHER PUBLICATIONS

Oguri et al, JP 2005-239560 Machine Translation, Sep. 8, 2005 (Year: 2005).*
International Search Report dated Jan. 24, 2017 in PCT/JP2016/005108, filed on Dec. 12, 2016.
Extended European Search Report dated Jul. 29, 2019 in Patent Application No. 16875117.0, citing document AA therein, 7 pages.

* cited by examiner

*Primary Examiner* — Jessica Whiteley
(74) *Attorney, Agent, or Firm* — Oblon, McClelland, Maier & Neustadt, L.L.P.

(57) ABSTRACT

The present invention provides a dental adhesive material kit excellent in storage stability of the materials and exhibiting excellent bond durability to dentin by photopolymerization. The present invention is a dental adhesive material kit comprising a dental aqueous adhesive composition (A) and a dental curable composition (B), wherein: the dental aqueous adhesive composition (A) comprises a (meth)acrylic polymerizable monomer (a) containing an acid group, a vanadium compound (b), water (c), a (meth)acrylic polymerizable monomer (d) containing an amino group, and a polymerization inhibitor (i); the content of the polymerization inhibitor (i) is 25 to 1000 parts by weight per 100 parts by weight of the vanadium compound (b); and the dental curable composition (B) comprises a (meth)acrylic polymerizable monomer (e) containing no acid group, a hydroperoxide (f), a photopolymerization initiator (g), and a filler (h) and does not comprise a thiourea compound.

10 Claims, No Drawings

DENTAL ADHESIVE MATERIAL KIT

TECHNICAL FIELD

The present invention relates to a dental adhesive material kit. The present invention particularly relates to a dental adhesive material kit comprising an aqueous adhesive composition and curable composition, excellent in storage stability, and exhibiting high bond durability to a tooth structure by photopolymerization.

BACKGROUND ART

Adhesive materials are used for restorative treatment of teeth. As the adhesive materials, resin-based curable compositions including, for example, a radical-polymerizable monomer and polymerization initiator are generally used.

Conventionally, two major proposals have been made for the resin-based curable compositions in order to improve their adhesiveness to a tooth structure. One of the proposals is related to a radical-polymerizable monomer containing an acid group and intended to improve chemical and physical interaction with a tooth structure to which the composition is adhered. The other is a proposal related to a polymerization initiator intended to efficiently polymerize and cure a curable composition including an acid group-containing radical-polymerizable monomer on a tooth structure.

As dental adhesive materials composed of these resin-based curable compositions, so-called self-etching adhesive materials are commonly used.

Specifically, a self-etching primer and/or bonding material including a polymerizable monomer containing an acid group and hydrophilic polymerizable monomer is applied onto the surface of a tooth structure.

To exhibit sufficient bond strength to a tooth structure, particularly dentin, dental adhesive materials need to cause demineralization effect in which the surface of dentin is dissolved with an acid component, penetration effect in which a polymerizable monomer component penetrates the collagen of dentin, and curing effect in which the penetrated polymerizable monomer component is cured to form a hybrid layer with the collagen.

However, when resin-based curable compositions are adhered to a tooth structure, curing inhibition by oxygen existing at the adhesive interface often decreases the degree of the curing effect among the above demineralization effect, penetration effect, and curing effect, which leads to a failure to obtain sufficient bond strength. Such curing inhibition is more salient when curable compositions are adhered to the dentin of a tooth including a lot of oxygen. Moreover, polymerization inhibition due to dissolved oxygen is particularly salient on the dentin in a root canal of a tooth because the dentin has a high water content.

In recent years, thanks to great progress of light irradiation units, photopolymerization allowing a short-time procedure has become used in restoration treatment with an abutment construction material to fill the inside of a root canal where light cannot reach easily for restoration. However, since light is applied from above and curing proceeds from the top of the filling material, strain and stress due to shrinkage caused by polymerization are likely to concentrate at the interface with a tooth structure to increase a risk of inducing detachment of the filling material.

Conventionally, first light irradiation is carried out after an adhesive material is applied, and second light irradiation is carried out after a filling material is placed. However, there is a growing demand for a system in which a primer is applied, a filling material is then placed without light irradiation of the primer, and photopolymerization is accomplished by one-time light irradiation. This system is exposed to an increased risk of inducing detachment of the filling material. A redox polymerization initiator adapted to the system and capable of effectively reducing the oxygen-induced curing inhibition at the interface with a tooth structure during curing to promote a polymerization and curing reaction has been proposed.

The adhesive kit described in Patent Literature 1 is an example in which high bond strength is achieved by incorporating a transition metal compound in a pretreatment agent and hydroperoxide and pyridylthiourea in an adhesive material. The dental restorative filling kit described in Patent Literature 2 is an example in which high bond strength and storage stability of the material are achieved by including a transition metal compound in a pretreatment agent and hydroperoxide in a filling material and excluding an amine from the pretreatment agent and an aryl borate compound from the filling material.

CITATION LIST

Patent Literature

Patent Literature 1: WO 2013/046648
Patent Literature 2: JP 2009-167132 A

SUMMARY OF INVENTION

Technical Problem

Patent Literature 1 states that the adhesive kit exhibits excellent bond strength by chemical polymerization; however, there is no description of bond strength achieved by light irradiation. For Patent Literature 2, it is conceivable that the pretreatment agent devoid of any amine tends to have a low pH, which causes excessive decalcification of a tooth structure, particularly dentin, and hence a decrease in bond durability. However, there is no description of bond durability in Patent Literature 2.

Therefore, the present invention aims to provide a dental adhesive material kit excellent in storage stability of the materials and exhibiting excellent bond durability to dentin by photopolymerization. The present invention particularly aims to provide a dental adhesive material kit excellent in storage stability of the materials and exhibiting excellent bond durability to dentin even by short-time light irradiation.

Solution to Problem

The present invention provides a dental adhesive material kit comprising a dental aqueous adhesive composition (A) and a dental curable composition (B), wherein the dental aqueous adhesive composition (A) comprises a (meth)acrylic polymerizable monomer (a) containing an acid group, a vanadium compound (b), water (c), a (meth)acrylic polymerizable monomer (d) containing an amino group, and a polymerization inhibitor (i), the content of the polymerization inhibitor (i) is 25 to 1000 parts by weight per 100 parts by weight of the vanadium compound (b), and the dental curable composition (B) comprises a (meth)acrylic polymerizable monomer (e) containing no acid group, a hydroperoxide (f), a photopolymerization initiator (g), and a filler (h) and does not comprise a thiourea compound.

The present invention also provides an abutment construction material kit comprising the dental adhesive material kit.

Advantageous Effects of Invention

The dental adhesive material kit of the present invention is excellent in storage stability of the materials and can achieve excellent bond durability to a tooth structure such as dentin. Particularly, the dental adhesive material kit of the present invention is excellent in storage stability of the materials and can achieve excellent bond durability to dentin even by short-time light irradiation.

DESCRIPTION OF EMBODIMENTS

The dental adhesive material kit of the present invention comprises a dental aqueous adhesive composition (A) and a dental curable composition (B), wherein: the dental aqueous adhesive composition (A) comprises a (meth)acrylic polymerizable monomer (a) containing an acid group, a vanadium compound (b), water (c), a (meth)acrylic polymerizable monomer (d) containing an amino group, and a polymerization inhibitor (i); the content of the polymerization inhibitor (i) is 25 to 1000 parts by weight per 100 parts by weight of the vanadium compound (b); and the dental curable composition (B) comprises a (meth)acrylic polymerizable monomer (e) containing no acid group, a hydroperoxide (f), a photopolymerization initiator (g), and a filler (h) and does not comprise a thiourea compound.

A detailed study by the present inventors revealed that not only is adhesiveness exhibited, but high bond durability and high storage stability of the materials can be obtained by a two-step curing system employing: an aqueous adhesive composition comprising a (meth)acrylic polymerizable monomer (a) containing an acid group which serves as a polymerization accelerator, vanadium compound (b) which serves as a reducing agent of a redox polymerization initiator, water (c), a (meth)acrylic polymerizable monomer (d) containing an amino group, and predetermined amount of a polymerization inhibitor (i); and a curable composition comprising a (meth)acrylic polymerizable monomer (e) containing no acid group, hydroperoxide (f) which serves as an oxidant of the redox polymerization initiator, photopolymerization initiator (g), and filler (h) and not comprising a thiourea compound.

First, the dental aqueous adhesive composition (A) will be described in detail. The aqueous adhesive composition (A) comprises the (meth)acrylic polymerizable monomer (a) containing an acid group. The (meth)acrylic polymerizable monomer (a) containing an acid group promotes decalcification of a tooth structure to improve adhesiveness to a tooth structure, and also promotes chemical polymerization at the adhesive interface. In the present specification, "(meth)acrylic" means "methacrylic" or "acrylic", and "(meth)acryloyl" means "methacryloyl" or "acryloyl".

Examples of the (meth)acrylic polymerizable monomer (a) containing an acid group include a (meth)acrylic polymerizable monomer having at least one acid group such as a phosphoric acid group, pyrophosphoric acid group, thiophosphoric acid group, phosphonic acid group, carboxylic acid group, or sulfonic acid group and having at least one (meth)acryloyl group. One (meth)acrylic polymerizable monomer (a) containing an acid group can be used alone, or two or more (meth)acrylic polymerizable monomers (a) containing an acid group can be used in appropriate combination. Specific examples of the (meth)acrylic polymerizable monomer (a) containing an acid group are as follows.

Examples of the (meth)acrylic polymerizable monomer containing a phosphoric acid group include: monofunctional phosphoric acid group-containing (meth)acrylates such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-methacryloyloxyethyl-(4-methoxyphenyl) hydrogen phosphate, and 2-methacryloyloxypropyl-(4-methoxyphenyl) hydrogen phosphate and their acid chlorides, alkali metal salts, and amine salts; and difunctional phosphoric acid group-containing (meth)acrylates such as bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, and 1,3-di(meth)acryloyloxypropyl dihydrogen phosphate and their acid chlorides, alkali metal salts, and amine salts.

Examples of the (meth)acrylic polymerizable monomer containing a pyrophosphoric acid group include bis[2-(meth)acryloyloxyethyl]pyrophosphate, bis[4-(meth)acryloyloxybutyl]pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and their acid chlorides, alkali metal salts, and amine salts.

Examples of the (meth)acrylic polymerizable monomer containing a thiophosphoric acid group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyeicosyl dihydrogen thiophosphate, and their acid chlorides, alkali metal salts, and amine salts.

Examples of the (meth)acrylic polymerizable monomer containing a phosphonic acid group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl phosphonoacetate, 10-(meth)acryloyloxydecyl phosphonoacetate, and their acid chlorides, alkali metal salts, and ammonium salts.

Examples of the (meth)acrylic polymerizable monomer containing a carboxylic acid group include: a monofunctional polymerizable monomer having one carboxyl group or acid anhydride group thereof per molecule; and a monofunctional polymerizable monomer having a plurality of (two or more) carboxyl groups or acid anhydride groups thereof per molecule.

Examples of the monofunctional polymerizable monomer having one carboxyl group or acid anhydride group thereof per molecule include (meth)acrylic acid, N-(meth)acryloylglycine, N-(meth)acryloylaspartic acid, 2-(meth)acryloyloxyethyl hydrogen succinate, 2-(meth)acryloyloxyethyl hydrogen phthalate, 2-(meth)acryloyloxyethyl hydrogen malate, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and compounds derived by converting the carboxyl group of the aforementioned compounds into an acid anhydride group.

Examples of the monofunctional polymerizable monomer having a plurality of carboxyl groups or acid anhydride groups thereof per molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, 6-(meth)acryloyloxyethyl-naphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, and 4-(meth)acryloyloxyethyl-naphthalene-1,8-tricarboxylic acid anhydride.

Examples of the (meth)acrylic polymerizable monomer containing a sulfonic acid group include 2-(meth)acrylamido-2-methylpropanesulfonic acid and 2-sulfoethyl (meth)acrylate.

Among the above (meth)acrylic polymerizable monomers (a) containing an acid group, one or more selected from the group consisting of 10-(meth)acryloyloxydecyl dihydrogen phosphate, 4-(meth)acryloyloxyethyl trimellitate anhydride, 4-(meth)acryloyloxyethyl trimellitate, 11-(meth)acryloyloxyundecane-1,1-dicarboxylic acid, and a mixture of 2-methacryloyloxyethyl dihydrogen phosphate and bis(2-methacryloyloxyethyl)hydrogen phosphate are preferred in that they make a good contribution to bond strength when used in an adhesive composition.

The content of the (meth)acrylic polymerizable monomer (a) containing an acid group in the aqueous adhesive composition (A) is preferably 1 to 45 parts by weight, more preferably 5 to 40 parts by weight, and even more preferably 10 to 38 parts by weight per 100 parts by weight of the total amount of the polymerizable monomers and solvents comprised in the aqueous adhesive composition (A). The total amount of the polymerizable monomers and solvents refers to the sum of the amounts of the (meth)acrylic polymerizable monomer (a) containing an acid group, water (c), (meth)acrylic polymerizable monomer (d) containing an amino group, organic solvent, and other polymerizable monomer (for example, the (meth)acrylic polymerizable monomer (e) containing no acid group). The content of a component per 100 parts by weight of the total amount of the polymerizable monomers and solvents refers to the content (weight %) of the component per 100 weight % of the sum of the amounts of the polymerizable monomers. Therefore, the sum of the contents of the components does not exceed 100 parts by weight.

The vanadium compound (b) is a component functioning as a reducing agent in redox polymerization. The vanadium compound (b) in the aqueous adhesive composition (A) is preferably a compound of tetravalent and/or pentavalent vanadium. As the compound of tetravalent and/or pentavalent vanadium, for example, divanadium(IV) tetroxide, vanadyl(IV) acetylacetonate, vanadyl(IV) oxalate, vanadyl (IV) sulfate, oxobis(1-phenyl-1,3-butanedionate)vanadium (IV), bis(maltolato)oxovanadium(IV), vanadium(V) pentoxide, sodium metavanadate(V), and ammonium metavanadate(V) are preferably used. Among these vanadium compounds, vanadyl(IV) acetylacetonate and bis(maltolato)oxovanadium(IV) are preferably used, and vanadyl(IV) acetylacetonate is most preferably used. One vanadium compound (b) can be used alone, or two or more vanadium compounds (b) can be used in combination.

The content of the vanadium compound (b) in the aqueous adhesive composition (A) is preferably 0.0001 parts by weight or more per 100 parts by weight of the total amount of the polymerizable monomers comprised in the aqueous adhesive composition (A), more preferably 0.0005 parts by weight or more, and even more preferably 0.001 parts by weight or more, because in this case, the curing rate is not reduced. The content of the vanadium compound (b) in the aqueous adhesive composition (A) is preferably 10 parts by weight or less per 100 parts by weight of the total amount of the polymerizable monomers, more preferably 5.0 parts by weight or less, and even more preferably 1.0 parts by weight or less, because in this case, a polymerization initiator residue cannot dissolve from a cured product of the adhesive composition.

The aqueous adhesive composition (A) of the present invention comprises water (c). Water (c) contributes to promoting penetration of the composition into a tooth structure. Water (c) also dissolves the (meth)acrylic polymerizable monomer (a) containing an acid group, vanadium compound (b), and hydroperoxide (f). That is, water (c) functions as a field where the substances contributing to initiating polymerization dissolve and react.

The content of water (c) in the aqueous adhesive composition (A) is preferably 5 to 75 parts by weight, more preferably 10 to 60 parts by weight, and even more preferably 15 to 45 parts by weight per 100 parts by weight of the total amount of the polymerizable monomers and solvents comprised in the aqueous adhesive composition (A).

The aqueous adhesive composition (A) of the dental adhesive material kit of the present invention comprises a (meth)acrylic polymerizable monomer (d) containing an amino group. The (meth)acrylic polymerizable monomer (d) containing an amino group is a component adjusting the pH of the aqueous adhesive composition. The (meth)acrylic polymerizable monomer (d) inhibits excessive decalcification to enable appropriate decalcification for penetration and curing particularly when the aqueous adhesive composition (A) is applied to dentin, and also increases the storage stability of the aqueous adhesive composition (A). The pH of the aqueous adhesive composition (A) is preferably less than 4.0, more preferably 1.2 to 3.5, and even more preferably 1.5 to 3.0.

Examples of the (meth)acrylic polymerizable monomer (d) containing an amino group include primary aminoalkyl (meth)acrylates, primary aminoalkyl (meth)acrylamides, secondary aminoalkyl (meth)acrylates, secondary aminoalkyl (meth)acrylamides, tertiary aminoalkyl (meth)acrylates, tertiary aminoalkyl (meth)acrylamides, primary aminophenyl (meth)acrylates, primary aminophenyl (meth)acrylamides, secondary aminophenyl (meth)acrylates, secondary aminophenyl (meth)acrylamides, tertiary aminophenyl (meth)acrylates, and tertiary aminophenyl (meth)acrylamides. One of these can be used alone, or two or more of these can be used in combination. Among these, the aminoalkyl (meth)acrylates are preferred because they form a stable water-soluble salt in the composition with the (meth)acrylic polymerizable monomer (a) containing an acid group and the salt exhibits excellent adhesiveness to a tooth structure. The tertiary aminoalkyl (meth)acrylates are more preferred in that polymerization inhibition and discoloration of a cured product are less likely to occur, and a monofunctional tertiary aminoalkyl (meth)acrylate is even more preferred.

Examples of the (meth)acrylic polymerizable monomer (d) containing an amino group include 2-(dimethylamino)ethyl (meth)acrylate, 2-(diethylamino)ethyl (meth)acrylate, 2-(dipropylamino)ethyl (meth)acrylate, 6-(diethylamino)hexyl (meth)acrylate, 6-(dimethylamino)hexyl (meth)acrylate, N-methyldiethanolamine di(meth)acrylate, and triethanolamine di(meth)acrylate. Among these, a tertiary amino group-containing (meth)acrylate is preferred because of its excellent curability, and a tertiary amino group-containing monofunctional (meth)acrylate such as 2-(dimethylamino)ethyl (meth)acrylate or 2-(diethylamino)ethyl (meth)acrylate is more preferred.

The content of the (meth)acrylic polymerizable monomer (d) containing an amino group in the aqueous adhesive composition (A) is preferably 0.1 to 20 parts by weight, more preferably 0.4 to 10 parts by weight, and even more preferably 1.0 to 6.0 parts by weight per 100 parts by weight of the total amount of the polymerizable monomers and solvents comprised in the aqueous adhesive composition (A). When the content of the (meth)acrylic polymerizable monomer (d) containing an amino group is 0.1 to 20 parts by weight, the adhesiveness and storage stability are maintained well.

The aqueous adhesive composition (A) may comprise the (meth)acrylic polymerizable monomer (e) containing no acid group. The (meth)acrylic polymerizable monomer (e) containing no acid group used in the present invention penetrates into a tooth structure to improve the degree of polymerization of a cured product and thus improve bond strength. As the (meth)acrylic polymerizable monomer (e) containing no acid group comprised in the aqueous adhesive composition (A), a hydrophilic (meth)acrylic polymerizable monomer (e1) containing no acid group is preferred. As the hydrophilic (meth)acrylic polymerizable monomer (e1) containing no acid group, a monofunctional hydrophilic (meth)acrylic polymerizable monomer is preferred. One (meth)acrylic polymerizable monomer (e) containing no acid group can be used alone, or two or more (meth)acrylic polymerizable monomers (e) containing no acid group can be used in combination.

The (meth)acrylic polymerizable monomer (e) containing no acid group means a polymerizable monomer containing no acid group (such as a phosphoric acid group, pyrophosphoric acid group, thiophosphoric acid group, phosphonic acid group, carboxylic acid group, or sulfonic acid group) and having at least one (meth)acryloyl group per molecule.

Examples of the (meth)acrylic polymerizable monomer (e) containing no acid group include (meth)acrylates, (meth)acrylamides, and (meth)acrylamide derivatives.

The (meth)acrylic polymerizable monomers (e) containing no acid group are roughly classified into polyfunctional monomers (polyfunctional (meth)acrylic polymerizable monomers) having a plurality of (two or more) (meth)acryloyl groups and monofunctional monomers (monofunctional (meth)acrylic polymerizable monomers) having one (meth)acryloyl group.

Examples of the polyfunctional (meth)acrylic polymerizable monomer include difunctional aromatic (meth)acrylates, difunctional aromatic (meth)acrylamide derivatives, difunctional aliphatic (meth)acrylates, difunctional aliphatic (meth)acrylamide derivatives, tri- or higher-functional (meth)acrylates, and tri- or higher-functional (meth)acrylamide derivatives. Specific examples of the (meth)acrylic polymerizable monomer (e) containing no acid group include those used in the dental curable composition (B) described later.

In the present specification, the hydrophilic (meth)acrylic polymerizable monomer (e1) containing no acid group means a hydrophilic radical-polymerizable monomer containing no acid group and having a solubility in water of 5 weight % or more at 25° C. The solubility is preferably 10 weight % or more and more preferably 30 weight % or more.

The hydrophilic (meth)acrylic polymerizable monomer (e1) containing no acid group may be a monofunctional hydrophilic (meth)acrylic polymerizable monomer (e1-1) containing no acid group, difunctional hydrophilic (meth)acrylic polymerizable monomer (e1-2) containing no acid group, or tri- or higher-functional hydrophilic (meth)acrylic polymerizable monomer (e1-3) containing no acid group.

Examples of the monofunctional hydrophilic (meth)acrylic polymerizable monomer (e1-1) containing no acid group include 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate, 2-hydroxybutyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methoxypolyethylene glycol (meth)acrylate, (meth)acryloylmorpholine, and diethyl (meth)acrylamide. Among these, 2-hydroxyethyl (meth)acrylate, 3-hydroxypropyl (meth)acrylate, glycerol mono(meth)acrylate, erythritol mono(meth)acrylate, methoxypolyethylene glycol (meth)acrylate, (meth)acryloylmorpholine, and diethyl(meth)acrylamide are preferred in view of improvement of the penetrability into the collagen layer of dentin, and 2-hydroxyethyl methacrylate is particularly preferred.

Examples of the difunctional hydrophilic (meth)acrylic polymerizable monomer (e1-2) containing no acid group include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, 1,2-bis(3-(meth)acryloyloxy-2-hydroxypropoxy)ethane, N,N'-ethylenebis(meth)acrylamide, N,N'-propylenebis(meth)acrylamide, butylenebis(meth)acrylamide, N,N'-(dimethyl)ethylenebis(meth)acrylamide, N,N'-diethyl-1,3-propylenebis(meth)acrylamide, bis[2-(2-methyl-(meth)acrylamino)ethoxycarbonyl]hexamethylenethamine, and 2,2,4-trimethylhexamethylene-1,6-bis(meth)acrylamide. Among these, glycerol di(meth)acrylate, 1,2-bis(3-methacryloyloxy-2-hydroxypropoxy)ethane, N,N'-propylenebis(meth)

acrylamide, N,N'-(dimethyl)ethylenebis(meth)acrylamide, and N,N'-diethyl-1,3-propylenebis(meth)acrylamide are preferred in view of improvement of the balance between the penetrability into the collagen layer of dentin and crosslinkability, and 1,2-bis(3-methacryloyloxy-2-hydroxypropoxy)ethane is more preferred.

Examples of the tri- or higher-functional hydrophilic (meth)acrylic polymerizable monomer (e1-3) containing no acid group include pentaerythritol tri(meth)acrylate, pentaerythritol tetra(meth)acrylate, dipentaerythritol tri(meth)acrylate, dipentaerythritol tetra(meth)acrylate, and dipentaerythritol penta(meth)acrylate. Among these, dipentaerythritol tetra(meth)acrylate and dipentaerythritol penta(meth)acrylate are preferred in view of improvement of the balance between the penetrability into the collagen layer of dentin and crosslinkability.

The content of the hydrophilic (meth)acrylic polymerizable monomer (e1) containing no acid group in the aqueous adhesive composition (A) is preferably 25 to 70 weight %, more preferably 28 to 60 weight %, and even more preferably 30 to 50 weight %. If the content of the monomer (e1) is 25 weight % or more, the effect of adding the monomer (e1) on improvement in adhesiveness can be achieved more saliently. Meanwhile, if the content of the monomer (e1) is 70 weight % or less, the ability of the aqueous adhesive composition (A) to decalcify a tooth structure can be exhibited at a high level without decreasing the effect of adding the monomer (e1).

In a preferred embodiment, the hydrophilic (meth)acrylic polymerizable monomer (e1) containing no acid group includes the monofunctional hydrophilic (meth)acrylic polymerizable monomer (e1-1) containing no acid group. In that case, the adhesiveness to a tooth structure, particularly the adhesiveness to dentin, is further improved.

The aqueous adhesive composition (A) of the dental adhesive material kit of the present invention comprises a polymerization inhibitor (i) to impart storage stability. The polymerization inhibitor (i) in the aqueous adhesive composition (A) used in the present invention prevents discoloration of the aqueous adhesive composition and a decline in the adhesiveness thereof and enhances the storage stability thereof.

Examples of the polymerization inhibitor (i) include phenol-based, phosphor-based, sulfur-based, and amine-based polymerization inhibitors, and a phenol-based polymerization inhibitor is preferably used. Specific examples include hydroquinone, hydroquinone monomethyl ether, 3,5-di-t-butyl-4-hydroxytoluene, 3,5-di-t-butyl-4-hydroxyanisole, and 4-t-butylpyrocatechol. Among these, hydroquinone monomethyl ether and 3,5-di-t-butyl-4-hydroxytoluene are preferably used in that they have no adverse effect on adhesiveness and a strong inhibitory effect on discoloration and gelation. One polymerization inhibitor (i) can be used alone, or two or more polymerization inhibitors (i) can be used in combination.

The content of the polymerization inhibitor (i) in the aqueous adhesive composition (A) is 25 to 1000 parts by weight, preferably 50 to 750 parts by weight, and more preferably 100 to 500 parts by weight per 100 parts by weight of the vanadium compound (b). If the content of the polymerization inhibitor (i) is 25 to 1000 parts by weight, the adhesiveness and storage stability are maintained well.

The aqueous adhesive composition (A) of the dental adhesive material kit of the present invention can comprise a photopolymerization initiator to impart photocurability. Examples of the photopolymerization initiator include those mentioned as examples of the photopolymerization initiator (g) of the dental curable composition (B) described later.

The aqueous adhesive composition (A) may comprise a filler in order to improve the spreadability and flowability. As the filler used in the aqueous adhesive composition (A), a fine particle filler having a primary particle diameter of 1 nm to 0.1 μm is preferred in terms of the spreadability and flowability. Specific examples of the fine particle filler include inorganic fillers such as "Aerosil OX 50", "Aerosil 50", "Aerosil 200", "Aerosil 380", "Aerosil R 972", and "Aerosil 130" (these are names of products manufactured by Nippon Aerosil Co., Ltd.).

A water-soluble organic solvent may be added to the aqueous adhesive composition (A) in order to improve the bond strength, spreadability, penetrability to a tooth structure, and solubility in water (c) of the (meth)acrylic polymerizable monomer (a) containing an acid group and (meth)acrylic polymerizable monomer (e) containing no acid group. As the water-soluble organic solvent, an organic solvent having a boiling point of 150° C. or less under ordinary pressure and having a water solubility at 25° C. of 5 weight % or more, preferably 30 weight % or more, and most preferably soluble in water at any ratio is commonly used. Among such organic solvents, a water-soluble organic solvent having a boiling point of 100° C. or less under ordinary pressure is preferred. Specific examples include ethanol, methanol, 1-propanol, isopropyl alcohol, acetone, methyl ethyl ketone, 1,2-dimethoxyethane, 1,2-diethoxyethane, and tetrahydrofuran.

The aqueous adhesive composition (A) preferably does not comprise a photopolymerization initiator so that it will be possible to complete photopolymerization by one-time light irradiation, although the present invention is not particularly limited in this respect. Specifically, light irradiation is skipped after application of the aqueous adhesive composition (A) and is carried out after use of the dental curable composition (B). Examples of the photopolymerization initiator include the photopolymerization initiator (g) comprised in the dental curable composition (B). The aqueous adhesive composition (A) may comprise the polymerization accelerator (j) (for example, an aromatic amine) comprised in the dental curable composition (B).

In the dental adhesive material kit of the present invention, the aqueous adhesive composition (A) is preferably of one-pack type to eliminate the need of mixing and increase the ease of handling.

Next, the dental curable composition (B) will be described.

The dental curable composition (B) comprises a (meth)acrylic polymerizable monomer (e) containing no acid group, hydroperoxide W, photopolymerization initiator (g), and filler (h).

As the (meth)acrylic polymerizable monomer (e) containing no acid group comprised in the dental curable composition (B), the above-described polyfunctional (meth)acrylic polymerizable monomer and monofunctional (meth)acrylic polymerizable monomer can be used, and the polyfunctional (meth)acrylic polymerizable monomer is preferred in that it contributes to high mechanical strength or high bond strength of the resulting dental curable composition. One (meth)acrylic polymerizable monomer (e) containing no acid group can be used alone, or two or more (meth)acrylic polymerizable monomers (e) containing no acid group can be used in combination.

Examples of the polyfunctional (meth)acrylic polymerizable monomer include aromatic difunctional (meth)acrylates, aromatic difunctional (meth)acrylamide derivatives, aliphatic difunctional (meth)acrylates, aliphatic difunctional (meth)acrylamide derivatives, tri- or higher-functional (meth)acrylates, and tri- or higher-functional (meth)acrylamide derivatives.

Examples of aromatic difunctional (meth)acrylic polymerizable monomers include 2,2-bis((meth)acryloyloxyphenyl)propane, 2,2-bis[4-(3-acryloyloxy-2-hydroxypropoxy) phenyl]propane, 2,2-bis[4-(3-methacryloyloxy-2-hydroxypropoxy)phenyl]propane (commonly called "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydiprop oxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, 1,4-bis(2-(meth)acryloyloxyethyl)pyromellitate, and (meth)acrylamide compounds derived by replacing the ester bond of the aforementioned compounds with an amide bond. Among these, 2,2-bis[4-(3-methacryloyloxy-2-hydroxypropoxy)phenyl]propane and 2,2-bis(4-methacryloyloxypolyethoxyphenyl)propane are preferred in that they contribute to high mechanical strength of the resulting dental curable composition. The 2,2-bis(4-methacryloyloxypolyethoxyphenyl)propane is preferably one in which the average number of moles of added ethoxy groups is 2.6 (commonly called "D2.6E").

Examples of aliphatic difunctional (meth)acrylic polymerizable monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylenebis(2-carbamoyloxyethyl) dimethacrylate (commonly called "UDMA"), 1,2-bis(3-methacryloyloxy-2-hydroxypropoxy)ethane, and (meth)acrylamide compounds the same as the preceding compounds derived by replacing the ester bond of the aforementioned compounds with an amide bond. Among these, glycerol di(meth)acrylate, triethylene glycol di(meth)acrylate, neopentyl glycol di(meth)acrylate, 2,2,4-trimethylhexamethylenebis(2-carbamoyloxyethyl) dimethacrylate, and 1,2-bis(3-methacryloyloxy-2-hydroxypropoxy)ethane are preferred in that they contribute to excellent handling properties of the resulting dental curable composition.

Examples of tri- or higher-functional (meth)acrylic polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol] tetramethacrylate, 1,7-diacryloyloxy-2,2,6,6-tetraacryloyloxymethyl-4-oxa-heptane, and (meth)acrylamide compounds the same as the preceding compounds derived by replacing the ester bond of the aforementioned compounds with an amide bond. Among these, N,N'-(2,2,4-trimethylhexamethylene)bis[2-(aminocarboxy)propane-1,3-diol]tetramethacrylate and trimethylolpropane tri(meth)acrylate are preferred in that they contribute to high mechanical strength of the resulting dental curable composition.

Examples of monofunctional (meth)acrylic polymerizable monomers include 2-hydroxyethyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-(2-hydroxyethyl) (meth)acrylamide, N,N-bis(2-hydroxyethyl) (meth)acrylamide, methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-(meth)acryloyloxypropyltrimethoxysilane, 11-(meth)acryloyloxyundecyltrimethoxysilane, and (meth)acrylamide compounds the same as the preceding (meth)acrylate compounds derived by replacing the ester bond of the aforementioned compounds with an amide bond. Among these, 2-hydroxyethyl (meth)acrylate, 3-hydroxypropyl (meth)acrylate, glycerol mono(meth)acrylate, and erythritol mono(meth)acrylate are preferred in that they contribute to high affinity of the resulting dental curable composition for a tooth structure and high bond strength of the resulting dental curable composition.

The content of the (meth)acrylic polymerizable monomer (e) containing no acid group in the curable composition (B) is preferably 80 to 100 parts by weight and more preferably 90 to 100 parts by weight, and may be 100 parts by weight per 100 parts by weight of the total amount of the polymerizable monomers comprised in the curable composition (B). The content of a polymerizable monomer per 100 parts by weight of the total amount of the polymerizable monomers refers to the content (weight %) of the polymerizable monomer per 100 weight % of the sum of the amounts of the polymerizable monomers. Therefore, the sum of the contents of the polymerizable monomers does not exceed 100 parts by weight.

The curable composition (B) may comprise the (meth)acrylic polymerizable monomer (a) containing an acid group, but preferably does not comprise the (meth)acrylic polymerizable monomer (a) containing an acid group in view of the stability of the hydroperoxide (f), although the present invention is not particularly limited in this respect.

The dental curable composition (B) of the dental adhesive material kit of the present invention comprises the hydroperoxide (f). The hydroperoxide (f) is an oxidant component of a redox polymerization initiator.

Examples of the hydroperoxide (f) include 1,1,3,3-tetramethylbutyl hydroperoxide, t-butyl hydroperoxide, cumene hydroperoxide, and diisopropylbenzene hydroperoxide. One hydroperoxide (f) can be used alone, or two or more hydroperoxides (0 can be used in combination.

Among these hydroperoxides (f), 1,1,3,3-tetramethylbutyl hydroperoxide is particularly preferred because it is excellent in polymerizability at the interface with a tooth structure.

The content of the hydroperoxide (f) in the curable composition (B) is preferably 0.1 to 10 parts by weight per 100 parts by weight of the total amount of the polymerizable monomers comprised in the curable composition (B). If the content is less than 0.1 parts by weight per 100 parts by weight of the total amount of the polymerizable monomers, curing may be slowed. Therefore, the content is more preferably 0.2 parts by weight or more. If the content is more than 10 parts by weigh per 100 parts by weight of the total amount of the polymerizable monomers, curing progresses too fast and thus high adhesiveness cannot be obtained. Therefore, the content is more preferably 7.5 parts by weight or less. Hence, from the above perspectives, the content of the hydroperoxide (f) is more preferably 0.2 to 7.5 parts by weight and even more preferably 0.3 to 5.0 parts by weight per 100 parts by weight of the total amount of the polymerizable monomers comprised in the curable composition (B).

Preferably, the curable composition (B) does not comprise a reducing agent. When the curable composition (B) comprises a reducing agent, the storage stability of the hydroperoxide (f) and the activity of the polymerization initiator at the interface with a tooth structure decrease, which weakens the bond strength.

It is essential for the curable composition (B) of the dental adhesive material kit of the present invention to comprise the photopolymerization initiator (g) in order to impart photocurability.

Examples of the photopolymerization initiator (g) include (bis)acylphosphine oxides, salts thereof, α-diketones, thioxanthones or quaternaryammonium salts thereof, ketals, coumarins, anthraquinones, benzoin alkyl ether compounds, and α-aminoketone compounds. One photopolymerization initiator (g) can be used alone, or two or more photopolymerization initiators (g) can be used in combination. Specific examples of the above examples include those described in WO 2008/087977. Examples of the (bis)acylphosphine oxides include acylphosphine oxides such as 2,4,6-trimethylbenzoydiphenylphosphine oxide, 2,6-dimethoxybenzoydiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoydiphenylphosphine oxide, benzoyldi-(2,6-dimethylphenyl)phosphonate, and their salts. Other examples include the bisacylphosphine oxides such as bis(2,6-dichlorobenzoynphenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and their salts. Examples of the α-diketones include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferred in that it shows maximum absorption at a wavelength in the visible region.

Among these photopolymerization initiators, at least one selected from the group consisting of the (bis)acylphosphine oxides, salts thereof, and α-diketones is preferably used. The use thereof contributes to obtaining a composition excellent in photocurability under visible or near-ultraviolet light irradiation and exhibiting sufficient photocurability by light irradiation using any light source selected from a halogen lamp, light-emitting diode (LED), and xenon lamp.

The photopolymerization initiator (g) may be used in combination with a known polymerization accelerator for the purpose of promoting photopolymerization. Thus, the curable composition (B) may comprise the polymerization accelerator 0).

The content of the photopolymerization initiator (g) in the curable composition (B) is not particularly limited, and is preferably 0.01 to 10 parts by weight, and more preferably 0.10 to 3.0 parts by weight per 100 parts by weight of the total amount of the polymerizable monomers comprised in the curable composition (B) in view of photocurability.

Examples of the polymerization accelerator (j) comprised in the curable composition (B) include amines, sulfinic acids, salts of sulfinic acids, borate compounds, barbituric acid derivatives, triazine compounds, tin compounds, copper compounds, halogen compounds, aldehydes, thiol compounds, sulfurous acid salts, and bisulfite salts.

Examples of the amines used as the polymerization accelerator (j) include aliphatic amines and aromatic amines. In the present specification, the (meth)acrylic polymerizable monomer (d) containing an amino group is not included in the amines as the polymerization accelerator (j). The curable composition (B), however, may comprise the (meth)acrylic polymerizable monomer (d) containing an amino group.

Examples of the aliphatic amines as the polymerization accelerator (j) include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methykliethanolamine, N-ethyldiethanolamine, N-n-butylodiethanolamine, N-lauryldiethanolamine, triethanolamine, trimethylamine, triethylamine, and tributylamine. Among these, the tertiary aliphatic amines are preferred in view of the curability and storage stability of the composition. Among the tertiary aliphatic amines, N-methyldiethanolamine and triethanolamine are more preferably used.

Examples of the aromatic amines as the polymerization accelerator (j) include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-ti-butylaniline, N,N-dimethylaniline, N,N-dimethyl-p-toluidine, N,N dimethyl m toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, 4-(N,N-dimethylamino)benzophenone, butyl 4-dimethylaminobenzoate, and 4-(dimethylamino)benzonitrile. Among these, at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone is preferably used in view of their ability to impart high curability to the composition.

The content of the polymerization accelerator (j) in the curable composition (B) is not particularly limited, and is preferably 0.01 to 5.0 parts by weight and more preferably 0.10 to 3.0 parts by weight per 100 parts by weight of the total amount of the polymerizable monomers comprised in the curable composition (B) in view of photocurability.

The curable composition (B) of the dental adhesive material kit of the present invention preferably comprises the filler (h) in order to increase the mechanical strength obtained after curing. Examples of the filler (h) include an inorganic filler, organic filler, and composite filler formed of an inorganic filler and organic filler. The average particle diameter of the filler (h) is not particularly limited, and is preferably 1 nm to 50 μm and more preferably 1 nm to 10 μm in view of, for example, obtaining sufficient mechanical strength. In the present specification, the average particle diameter of the filler means the average particle diameter (average primary particle diameter) of primary particles of the filler.

In the present specification, the average particle diameter of the filler (h) can be determined by laser diffraction scattering method or by electron microscope observation of the particles. Specifically, the laser diffraction scattering method is convenient for particle diameter measurement on particles with a diameter of 0.1 μm or more, and electron microscope observation is convenient for particle diameter measurement on ultrafine particles with a diameter of less than 0.1 μm. The particle diameter of 0.1 μm is a value determined by the laser diffraction scattering method.

To be specific about the laser diffraction scattering method, for example, the average particle diameter can be measured using a 0.2% aqueous solution of sodium hexametaphosphate as a dispersion medium by means of a laser diffraction particle size distribution analyzer (SALD-2100 manufactured by Shimadzu Corporation).

Examples of the inorganic filler include: silica; silica-based minerals, such as kaolin, clay, isinglass, and mica; and silica-based ceramics and glasses containing $Al_2O_3$, $B_2O_3$, $TiO_2$, $ZrO_2$, BaO, $La_2O_3$, SrO, ZnO, CaO, $P_2O_5$, $Li_2O$, $Na_2O$, etc. As the glasses, lanthanum glass, barium glass, strontium glass, soda glass, lithium borosilicate glass, zinc glass, fluoroaluminosilicate glass, borosilicate glass, and bio glass are suitably used. Crystalline quartz, hydroxyapatite, alumina, titanium oxide, yttrium oxide, zirconia, calcium phosphate, barium sulfate, aluminum hydroxide, sodium fluoride, potassium fluoride, sodium monofluorophosphate, lithium fluoride, and ytterbium fluoride are also suitably used.

Examples of the organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer.

Examples of the composite filler formed of an inorganic filler and organic filler include: a composite filler obtained by dispersing an inorganic filler in an organic filler; and an inorganic-organic composite filler obtained by coating an inorganic filler with any of various polymers.

Before used, the filler (h) may be preliminarily subjected to surface treatment with a commonly-known surface treatment agent such as a silane coupling agent in order to improve the curability, mechanical strength, and spreadability. Examples of the surface treatment agent include vinyltrimethoxysilane, vinyltriethoxysilane, vinyltrichlorosilane, vinyltris(2-methoxyethoxy)silane, 3-methacryloyloxypropyltrimethoxysilane, 3-glycidoxypropyltrimethoxysilane, 3-mercaptopropyltrimethoxysilane, and 3-aminopropyltriethoxysilane.

One filler (h) may be added alone, or two or more fillers (h) may be added in combination.

As the filler (h) used in the curable composition (B), silica, lanthanum glass, barium glass, strontium glass, soda glass, lithium borosilicate glass, zinc glass, fluoroaluminosilicate glass, borosilicate glass, bioglass, crystalline quartz, alumina, titanium oxide, yttrium oxide, and zirconia are preferred.

The content of the filler (h) in the curable composition (B) is not particularly limited, and is preferably 50 to 500 parts by weight and more preferably 100 to 400 parts by weight per 100 parts by weight of the total amount of the polymerizable monomers comprised in the curable composition (B) in view of mechanical strength and handling properties. The content of the filler (h) in the curable composition (B) is not particularly limited, and is preferably 55 to 90 weight %, more preferably 60 to 88 weight %, and even more preferably 65 to 85 weight % with respect to the total weight of the curable composition (B) in view of mechanical strength. The total weight of the curable composition (B) refers to the total weight of all components such as the polymerizable monomer, polymerization initiator, solvent, polymerization accelerator, polymerization inhibitor, filler, water-soluble fluoride compound, and additive which are comprised in the composition.

The curable composition (B) of the dental adhesive material kit of the present invention does not comprise a thiourea compound in order not to decrease the storage stability.

Examples of the thiourea compound include an acyclic thiourea compound and cyclic thiourea compound.

Examples of the acyclic thiourea compound include thiourea; $C_1$ to $C_{12}$ alkylthiourea compounds such as methylthiourea, ethylthiourea, N,N'-dimethylthiourea, N,N'-diethylthiourea, N,N'-di-n-propylthiourea, trimethylthiourea, triethylthiourea, tri-n-propylthiourea, tetramethylthiourea, tetraethylthiourea, and tetra-n-propylthiourea; $C_3$ to $C_{10}$ cycloalkylthiourea compounds such as N,N'-dicyclohexylthiourea and tricyclohexylthiourea; heterocyclic group-containing (suitably a heterocycle including a nitrogen atom) thiourea compounds such as 1-(2-pyridyl)-2-thiourea; and aromatic group-containing thiourea compounds such as N-benzoylthiourea.

Examples of the cyclic thiourea compound include a compound represented by the following formula (I).

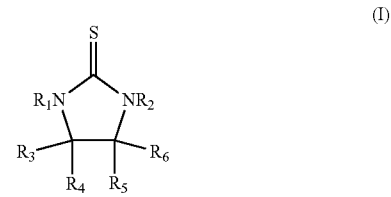

In this formula, $R_1$, $R_2$, $R_1$, $R_4$, $R_5$, and $R_6$ each independently represent a hydrogen atom, optionally substituted alkyl group, optionally substituted cycloalkyl group, optionally substituted alkoxy group, optionally substituted aryl group, optionally substituted acyl group, optionally substituted alkenyl group, optionally substituted aralkyl group, or optionally substituted monovalent heterocyclic group containing an oxygen atom, sulfur atom, or nitrogen atom (except for the case where all of $R_1$, $R_2$, $R_1$, $R_4$, $R_5$, and $R_6$ are hydrogen atoms), and $R_4$ and $R_5$ may form an optionally substituted ring with carbon atoms to which $R_4$ and $R_5$ are bonded.

The alkyl group represented by $R_1$ to $R_6$ may be linear or branched. Examples of the alkyl group represented by $R_1$ to $R_6$ include a methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, n-heptyl group, n-octyl group, 2-ethylhexyl group, n-nonyl group, and n-decyl group. Examples of the cycloalkyl group represented by $R_1$ to $R_6$ include a cyclopropyl group, cyclobutyl group, cyclopentyl group, cyclohexyl group, cycloheptanyl group, cyclooctanyl group, and cyclononanoyl group. Examples of the alkoxy group represented by $R_1$ to $R_6$ include a propoxy group, isopropoxy group, n-butoxy group, t-butoxy group, pentyloxy group, and hexyloxy group.

Examples of the substituent optionally contained in the alkyl group, cycloalkyl group, alkoxy group, acyl group, and alkenyl group include a halogen atom (e.g., a chlorine atom and bromine atom), aryl group (e.g., a phenyl group and naphthyl group), and monovalent heterocyclic group (e.g., a pyridyl group and imidazolyl group). The number of the substituents is preferably 1 or 2. Examples of the substituent optionally contained in the aryl group, aralkyl group, and monovalent heterocyclic group include a halogen atom (e.g., a chlorine atom and bromine atom), alkyl group (e.g., a methyl group and ethyl group), alkoxy group (e.g., a methoxy group and ethoxy group), aryl group (e.g., a phenyl group and naphthyl group), and monovalent heterocyclic group (e.g., a pyridyl group and imidazolyl group).

$R_4$ and $R_5$ may form an optionally substituted ring with carbon atoms to which $R_4$ and $R_5$ are bonded. Examples of such a ring include a cyclobutyl ring, cyclopentyl ring, and cyclohexyl ring. Examples of the substituent the ring may contain include a halogen atom (e.g., a chlorine atom and bromine atom), aryl group (e e.g., a phenyl group and naphthyl group), and monovalent heterocyclic group (e.g., a pyridyl group and imidazolyl group).

As $R_1$ and $R_2$, a hydrogen atom, alkyl group, cycloalkyl group, aryl group, alkenyl group, and aralkyl group are preferred.

Specific examples of the above cyclic thiourea compound include 4-methyl-2-imidazolidinethione, 4,4-dimethyl-2-imidazolidinethione, 4,5-dimethyl-2-imidazolidinethione, 4-ethyl-2-imidazolidinethione, 4,4-diethyl-2-imidazolidinethione, 4,5-diethyl-2-imidazolidinethione, 4,4,5-trimethyl-2-imidazolidinethione, and 4,4,5,5-tetramethyl-2-imidazolidinethione.

The curable composition (B) of the dental adhesive material kit of the present invention is preferably of a one-pack type in view of the ease of handling.

A known water-soluble fluoride compound releasing fluorine ion may be added to the aqueous adhesive composition (A) and/or curable composition (B) of the dental adhesive material kit of the present invention in such an amount that the adhesiveness is not decreased. Examples of the water-soluble fluoride compound include lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminum fluoride, manganese fluoride, copper fluoride, lead fluoride, silver fluoride, antimony fluoride, cobalt fluoride, bismuth fluoride, tin fluoride, diammine silver fluoride, sodium monofluorophosphate, potassium fluorotitanate, fluorostannate, and fluorosilicate. One water-soluble fluoride compound may be used alone, or two or more water-soluble fluoride compounds may be used in combination. It is preferable that before added, the water-soluble fluoride compound be micronized by a method described in, for example, JP 02-258602 A or be coated with polysiloxane by a method described in JP 10-036116 A.

The curable composition (B) preferably does not comprise a vanadium compound, although the present invention is not particularly limited in this respect. Examples of the vanadium compound include those mentioned as examples of the vanadium compound (b) of the aqueous adhesive composition (A). The curable composition (B) is preferably a non-aqueous curable composition free of water in view of mechanical strength.

A known additive can be added to the aqueous adhesive composition (A) and curable composition (B) of the dental adhesive material kit of the present invention as long as the performance is not degraded. Examples of such an additive include a polymerization inhibitor, antioxidant, pigment, dye, ultraviolet absorber, organic solvent, and thickener. As the polymerization inhibitor, those mentioned as examples of the polymerization inhibitor (i) comprised in the aqueous adhesive composition (A) can be used.

An example of a preferred embodiment of the aqueous adhesive composition (A) will be given. The aqueous adhesive composition (A) preferably comprises 1 to 45 parts by weight of the component (a), 5 to 75 parts by weight of the component (c), and 0.1 to 20 parts by weight of the component (d) per 100 parts by weight of the total amount of the polymerizable monomers and solvents, and preferably comprises 0.0001 to 5.0 parts by weight of the component (b) per 100 parts by weight of the total amount of the polymerizable monomers.

An example of a preferred embodiment of the curable composition (B) will be given. The curable composition (B) preferably comprises 80 to 100 parts by weight of the component (e) per 100 parts by weight of the total amount of the polymerizable monomers, and preferably comprises 0.1 to 10 parts by weight of the component (f), 0.01 to 10 parts by weight of the component (g), and 50 to 500 parts by weight of the component (h) per 100 parts by weight of the total amount of the polymerizable monomers.

Conditions such as the type and content of each component in the aqueous adhesive composition (A) and curable composition (B) of the above preferred embodiments can be selected and changed appropriately to the extent described in the present specification.

The dental adhesive material kit of the present invention can exhibit excellent bond durability and is excellent in storage stability. Particularly, the dental adhesive material kit of the present invention can achieve excellent bond durability by short-time light irradiation and can achieve excellent adhesiveness even when employed to fill a deep part of a root canal. The light irradiation time for the case of using the dental adhesive material kit of the present invention is not particularly limited, and may be 15 seconds or less, or 10 seconds or less. When used for restorative treatment of a root canal, the dental 1 adhesive material kit offers the following advantages thanks to the fact that the aqueous adhesive composition (A) and curable composition (B) are chemically polymerized by contact with each other: curing is successfully accomplished even in such a deep part of the root canal that light does not reach; a strain and stress due to shrinkage caused by polymerization are prevented from concentrating at the interface with a tooth structure; and excellent bond durability can be achieved by short-time light irradiation. Therefore, the dental adhesive material kit of the present invention is preferably used as a dental abutment construction material kit for filling a root canal to a large depth. That is, the dental abutment construction material kit of the present invention comprises the dental aqueous adhesive composition (A) and dental curable composition (B).

EXAMPLES

Hereinafter, the present invention will be described based on Examples and Comparative Examples. However, the present invention is not limited to such examples in any respect. The abbreviations used hereinafter are listed below.

[(Meth)acrylic polymerizable monomer (a) containing an acid group]
MDP: 10-methacryloyloxydecyl dihydrogen phosphate
4-META: 4-methacryloyloxyethyl trimellitate anhydride

[Vanadium Compound (b)]
VOAA: Vanadyl(IV) acetylacetonate
BMOV: Bis(maltolato)oxovanadium(IV)

[Water (c)]
Purified water

[(Meth)Acrylic Polymerizable Monomer (d) Containing an Amino Group]
DMAEMA: 2-(diethylamino)ethyl methacrylate
TEADM: Triethanolamine dimethacrylate

[(Meth)acrylic polymerizable monomer (e) containing no acid group]
HEMA: 2-hydroxyethyl methacrylate
GDEMA: 1,2-bis(3-methacryloyloxy-2-hydroxypropoxy)ethane
TEGDMA: Triethylene glycol dimethacrylate
Bis-GMA: 2,2-bis[4-(3-methacryloyloxy-2-hydroxypropoxy)phenyl]propane
D2.6E: 2,2-bis(4-methacryloyloxypolyethoxyphenyl)propane (A compound in which the average number of moles of added ethoxy groups is 2.6.)

[Hydroperoxide (f)]
THP: 1,1,3,3-tetramethylbutyl hydroperoxide
CHP: Cumene hydroperoxide

[Photopolymerization initiator (g)]
CQ: Dl-camphorquinone
BAPO: Bis(2,4,6-trimethylbenzoy)phenylphosphine oxide

[Filler (h)]
A filler 1 and filler 2 can be obtained in accordance with the following production methods. In the following production methods, "room temperature" means 25° C.

Filler 1: 3-methacryloyloxypropyltrimethoxysilane-treated barium glass powder

Barium glass ("RAY-SORB E-3000" manufactured by Esstech, Inc.) was pulverized with a vibrating ball mill to obtain barium glass powder. In a 500-mL one-necked eggplant flask were put 100 g of the obtained barium glass powder, 0.5 g (0.5 parts by weight per 100 parts by weight of the filler) of 3-methacryloyloxypropyltrimethoxysilane ("KBM-503" manufactured by Shin-Etsu Silicones), and 200 mL of toluene, which were stirred together at room temperature for 2 hours. Subsequently, the toluene was distilled off under reduced pressure, followed by vacuum drying at 40° C. for 16 hours and then by vacuum drying at 90° C. for 3 hours. Thus, 3-methacryloyloxypropyltrimethoxysilane-treated barium glass powder (filler 1) was obtained. The average particle diameter of the filler (1), as measured with a laser diffraction particle size distribution analyzer (manufactured by Shimadzu Corporation, product code: "SALD-2100", dispersion medium: 0.2% aqueous solution of sodium hexametaphosphate), was 2.4 μm.

Filler 2: 3-methacryloyloxypropyltrimethoxysilane-treated colloidal silica powder The same treatment as that for the filler 1 was carried out except for using colloidal silica ("Aerosil OX 50" manufactured by Nippon Aerosil Co., Ltd., average particle diameter: 40 nm) instead of the barium glass ("RAY-SORB E-3000" manufactured by Esstech, Inc.) to obtain 3-methacryloyloxypropyltrimethoxysilane-treated colloidal silica powder (filler 2).

[Polymerization Inhibitor (i)]
BHT: 2,6-di-t-butyl-4-methylphenol
MEHQ: Hydroquinone monomethyl ether

[Polymerization accelerator (j)]
PDE: Ethyl 4-(N,N-dimethylamino)benzoate
DEPT: N,N-bis(2-hydroxyethyl)-p-toluidine
TEA: Triethanolamine

[Polymerization Accelerator Other than the Polymerization Accelerator (j)]
PTU: 1-(2-pyridyl)-2-thiourea Examples 1 to 16 and Comparative Examples 1 to 8 The raw materials shown in Tables 1 to 3 were mixed at ordinary temperature (25° C.) to prepare primers (aqueous adhesive compositions (A)) and pastes (dental curable compositions (B)). After stored for 1 day and 1 year at 25° C., the primers and pastes were examined for their properties according to the method in Test Example 1 below. Tables 1 to 3 show the results. The pH of the each aqueous adhesive composition (A) was measured just after the preparation of the composition using a glass electrode formed using a potassium chloride solution and a pH meter (for example, LAQUA twin, a compact pH meter manufactured by HORIBA, Ltd.).

Test Example 1 [Test for Tensile Bond Strength]

The labial surface of a bovine mandibular incisor was ground with #80 silicon carbide paper (manufactured by NIHON KENSHI CO., LTD.) under running water to form a flat dentin surface. The flat surface was further ground with #1000 silicon carbide paper (manufactured by NIHON KENSHI CO., LTD.) under running water to form a flat and smooth surface. To the flat and smooth surface was attached a 3-cm-thick and about 1-cm-square silicone rubber on which a double-faced tape having a circular hole of 4-mm-diameter was put to define the area and thickness over which materials are applied. The aqueous adhesive composition (A) prepared above was applied within the circular hole with a brush and left for 20 seconds, after which the applied aqueous adhesive composition (A) was dried by blowing air over the surface until losing its flowability. Next, the dental curable composition (B) was filled in the circular hole and a 1-cm-square PET film was press-bonded thereto. After that, the dental curable composition (B) was cured by 10-second light irradiation with a dental visible light irradiation unit (Pencure 2000 manufactured by Morita Corporation). Thereafter, the PET film was removed and the surface to which the film had been press-bonded was subjected to alumina sandblasting at a pressure of 2 MPa to roughen the surface of the cured product of the dental curable composition (B). To the roughened surface was adhered an end face (circular cross section) of a cylindrical stainless steel rod (diameter: 7 mm, length: 2.5 cm) using a commercially-available dental resin cement (PANAMA 21 manufactured by Kuraray Noritake Dental Inc.) to obtain an adhesion test sample. After the adhesion, the sample was allowed to stand at room temperature for 30 minutes and then immersed in distilled water. There were produced 10 such adhesion test samples. All samples immersed in distilled water were stored in a thermostat maintained at 37° C. After 24 hours, the samples were taken out from water and measured for their tensile bond strength using a universal testing machine (manufactured by Shimadzu Corporation). The tensile bond strength was measured with the crosshead speed set to 2 mm/min. The average of measurement values of 5 samples was determined as the tensile bond strength.

The other 5 samples adhered to the dentin were further subjected to thermal cycling (TC) in which the samples were subjected to 4000 cycles of alternate immersion in a 4° C. water bath and 60° C. water bath for 1 minute each, and then measured for the tensile bond strength. The tensile bond strength determined after the thermal cycling was employed to evaluate the bond durability. Tables 1 to 3 show the results.

TABLE 1

| | | | | Examples | | | | | | | |
|---|---|---|---|---|---|---|---|---|---|---|---|
| | | | | 1 | 2 | 3 | 4 | 5 | 6 | 7 | 8 |
| Raw material (parts by weight) | Aqueous adhesive composition (A) | MDP | (a)-1 | 20 | 20 | 20 | 20 | 20 | 10 | 30 | |
| | | 4-META | (a)-2 | | | | | | | | 20 |
| | | DMAEMA | (d)-1 | 3 | 1 | 5 | 3 | 3 | 3 | 3 | |
| | | TEADM | (d)-2 | | | | | | | | 3 |
| | | HEMA | (e)-1 | 30 | 30 | 30 | 30 | 30 | 40 | 20 | |
| | | GDEMA | (e)-2 | | | | | | | | 30 |
| | | VOAA | (b)-1 | 0.5 | 0.5 | 0.5 | 0.1 | 1.0 | 0.5 | 0.5 | |
| | | BMOV | (b)-2 | | | | | | | | 0.5 |
| | | Purified water | (c) | 32 | 34 | 30 | 32 | 32 | 32 | 32 | 32 |
| | | BHT | (i)-1 | 1.5 | 1.5 | 1.5 | 0.5 | 2.0 | 1.5 | 1.5 | 1.0 |
| | | MEHQ | (i)-2 | | | | | | | | 0.1 |
| | Curable composition (B) | GDEMA | (e)-2 | 20 | 20 | 20 | 20 | 20 | 20 | 20 | 20 |
| | | TEGDMA | (e)-3 | 10 | 10 | 10 | 10 | 10 | 10 | 10 | 10 |
| | | Bis-GMA | (e)-4 | 50 | 50 | 50 | 50 | 50 | 50 | 50 | 50 |
| | | D2.6E | (e)-5 | 20 | 20 | 20 | 20 | 20 | 20 | 20 | 20 |
| | | THP | (f)-1 | 3.0 | 3.0 | 3.0 | 3.0 | 3.0 | 3.0 | 3.0 | 3.0 |
| | | CQ | (g)-1 | 0.5 | 0.5 | 0.5 | 0.5 | 0.5 | 0.5 | 0.5 | 0.5 |
| | | Filler 1 | (h)-1 | 300 | 300 | 300 | 300 | 300 | 300 | 300 | 300 |
| | | Filler 2 | (h)-2 | 20 | 20 | 20 | 20 | 20 | 20 | 20 | 20 |
| | | BHT | (i)-1 | 0.1 | 0.1 | 0.1 | 0.1 | 0.1 | 0.1 | 0.1 | 0.1 |
| | | PDE | (j)-1 | 1.0 | 1.0 | 1.0 | 1.0 | 1.0 | 1.0 | 1.0 | 1.0 |
| Properties | | pH of aqueous adhesive composition (A) | | 2.0 | 1.8 | 2.5 | 2.0 | 2.0 | 2.7 | 1.5 | 2.0 |
| | | After preparation and storage for 1 day at 25° C. | | | | | | | | | |
| | | Tensile bond strength: after 24 hours (MPa) | | 18.5 | 18.7 | 17.3 | 17.1 | 19.1 | 17.2 | 18.2 | 16.8 |
| | | Tensile bond strength: after 4000 cycles of TC (MPa) | | 18.4 | 18.3 | 17.4 | 17.0 | 19.3 | 16.8 | 18.3 | 16.8 |
| | | After preparation and storage for 1 year at 25° C. | | | | | | | | | |
| | | Tensile bond strength: after 24 hours (MPa) | | 18.3 | 17.0 | 17.6 | 17.2 | 16.8 | 17.0 | 17.1 | 16.6 |
| | | Tensile bond strength: after 4000 cycles of TC (MPa) | | 18.2 | 17.1 | 17.5 | 17.1 | 16.5 | 16.7 | 16.9 | 16.5 |

TABLE 2

| | | | | Examples | | | | | | | |
|---|---|---|---|---|---|---|---|---|---|---|---|
| | | | | 9 | 10 | 11 | 12 | 13 | 14 | 15 | 16 |
| Raw material (parts by weight) | Aqueous adhesive composition (A) | MDP | (a)-1 | 20 | 20 | 20 | 20 | 20 | 20 | 20 | 20 |
| | | DMAEMA | (d)-1 | 3 | 3 | 3 | 3 | 3 | 3 | 3 | 3 |
| | | HEMA | (e)-1 | 30 | 30 | 30 | 30 | 30 | 30 | 30 | 30 |
| | | VOAA | (b)-1 | 0.5 | 0.5 | 0.5 | 0.5 | 0.5 | 0.5 | 0.5 | 0.5 |
| | | Purified water | (c) | 32 | 32 | 32 | 32 | 32 | 32 | 32 | 32 |
| | | BHT | (i)-1 | 1.5 | 1.5 | 1.5 | 1.5 | 1.5 | 1.5 | 1.5 | 1.5 |
| | Curable composition (B) | GDEMA | (e)-2 | 20 | 20 | 20 | 20 | 20 | 20 | 20 | 10 |
| | | TEGDMA | (e)-3 | 10 | 10 | 10 | 10 | 10 | 10 | 10 | 20 |
| | | Bis-GMA | (e)-4 | 50 | 50 | 50 | 50 | 50 | 50 | 50 | 20 |
| | | D2.6E | (e)-5 | 20 | 20 | 20 | 20 | 20 | 20 | 20 | 50 |
| | | THP | (f)-1 | 1.0 | 5.0 | 3.0 | 3.0 | 3.0 | 3.0 | | 3.0 |
| | | CHP | (f)-2 | | | | | | | 3.0 | |
| | | CQ | (g)-1 | 0.5 | 0.5 | 0.1 | 2.0 | 0.5 | 0.5 | 0.5 | 0.5 |
| | | BAPO | (g)-2 | | | | | | | | 0.5 |
| | | Filler 1 | (h)-1 | 300 | 300 | 300 | 300 | 200 | 400 | 300 | 300 |
| | | Filler 2 | (h)-2 | 20 | 20 | 20 | 20 | 40 | 10 | 20 | 20 |
| | | BHT | (i)-1 | 0.1 | 0.1 | 0.1 | 0.1 | 0.1 | 0.1 | 0.1 | 0.1 |
| | | PDE | (j)-1 | 1.0 | 1.0 | 0.5 | 3.0 | 1.0 | 1.0 | 1.0 | 1.0 |
| Properties | | pH of aqueous adhesive composition (A) | | 2.0 | 2.0 | 2.0 | 2.0 | 2.0 | 2.0 | 2.0 | 2.0 |
| | | After preparation and storage for 1 day at 25° C. | | | | | | | | | |
| | | Tensile bond strength: after 24 hours (MPa) | | 17.8 | 18.1 | 16.6 | 18.2 | 18.2 | 18.4 | 17.2 | 17.6 |
| | | Tensile bond strength: after 4000 cycles of TC (MPa) | | 17.6 | 17.8 | 16.5 | 18.0 | 18.1 | 18.1 | 17.1 | 17.5 |
| | | After preparation and storage for 1 year at 25° C. | | | | | | | | | |
| | | Tensile bond strength: after 24 hours (MPa) | | 17.6 | 18.2 | 16.1 | 18.3 | 18.1 | 18.3 | 17.4 | 17.4 |
| | | Tensile bond strength: after 4000 cycles of TC (MPa) | | 17.4 | 18.3 | 16.0 | 18.4 | 18.3 | 18.3 | 17.3 | 17.3 |

TABLE 4

| | | | | Comparative Examples | | | | | | | |
|---|---|---|---|---|---|---|---|---|---|---|---|
| | | | | 1 | 2 | 3 | 4 | 5 | 6 | 7 | 8 |
| Raw material | Aqueous adhesive | MDP | (a)-1 | 20 | 20 | 20 | 20 | 20 | 20 | 20 | 20 |
| | | DMAEMA | (d)-1 | 3 | | | | 3 | 3 | 3 | 3 |

TABLE 4-continued

|  |  |  |  | Comparative Examples | | | | | | | |
|---|---|---|---|---|---|---|---|---|---|---|---|
|  |  |  |  | 1 | 2 | 3 | 4 | 5 | 6 | 7 | 8 |
| (parts by weight) | composition (A) | HEMA | (e)-1 | 30 | 30 | 30 | 30 | 30 | 30 | 30 | 30 |
|  |  | VOAA | (b)-1 | 0.5 | 0.5 | 0.5 | 0.5 |  | 0.5 | 0.5 | 0.5 |
|  |  | Purified water | (c) | 32 | 32 | 32 | 32 | 32 | 32 | 32 | 32 |
|  |  | BHT | (i)-1 | 1.5 | 1.5 | 1.5 | 1.5 | 1.5 | 0.05 | 1.5 | 1.5 |
|  |  | DEPT |  |  |  |  | 3 |  |  |  |  |
|  |  | TEA |  |  |  |  |  | 3 |  |  |  |
|  | Curable composition (B) | GDEMA | (e)-2 | 20 | 20 | 20 | 20 | 20 | 20 | 20 | 20 |
|  |  | TEGDMA | (e)-3 | 10 | 10 | 10 | 10 | 10 | 10 | 10 | 10 |
|  |  | Bis-GMA | (e)-4 | 50 | 50 | 50 | 50 | 50 | 50 | 50 | 50 |
|  |  | D2.6E | (e)-5 | 20 | 20 | 20 | 20 | 20 | 20 | 20 | 20 |
|  |  | THP | (f)-1 | 3.0 | 3.0 | 3.0 | 3.0 | 3.0 | 3.0 |  | 3.0 |
|  |  | CQ | (g)-1 | 0.5 | 0.5 | 0.5 | 0.5 | 0.5 | 0.5 | 0.5 |  |
|  |  | Filler 1 | (h)-1 | 300 | 300 | 300 | 300 | 300 | 300 | 300 | 300 |
|  |  | Filler 2 | (h)-2 | 20 | 20 | 20 | 20 | 20 | 20 | 20 | 20 |
|  |  | BHT | (i)-1 | 0.1 | 0.1 | 0.1 | 0.1 | 0.1 | 0.1 | 0.1 | 0.1 |
|  |  | PDE | (j)-1 | 1.0 | 1.0 | 1.0 | 1.0 | 1.0 | 1.0 | 1.0 | 1.0 |
|  |  | PTU |  | 0.01 |  |  |  |  |  |  |  |
| Properties | | pH of aqueous adhesive composition (A) | | 2.0 | 1.1 | 1.8 | 2.3 | 2.0 | 2.0 | 2.0 | 2.0 |
| | | After preparation and storage for 1 day at 25° C. | | | | | | | | | |
| | | Tensile bond strength: after 24 hours (MPa) | | 18.2 | 18.1 | 13.2 | 12.7 | 3.2 | 18.3 | 7.8 | 0.0 |
| | | Tensile bond strength: after 4000 cycles of TC (MPa) | | 18.3 | 12.4 | 12.8 | 11.3 | 0.5 | 18.4 | 5.4 | 0.0 |
| | | After preparation and storage for 1 year at 25° C. | | | | | | | | | |
| | | Tensile bond strength: after 24 hours (MPa) | | Solidified | 13.2 | 11.3 | 10.5 | 1.9 | 10.3 | 7.4 | 0.0 |
| | | Tensile bond strength: after 4000 cycles of TC (MPa) | | Solidified | 9.8 | 10.9 | 10.0 | 0.1 | 9.4 | 4.8 | 0.0 |

The results in Tables 1 to 3 indicate that when the curable compositions are applied to a certain thickness, the dental adhesive material kits of the present invention show excellent adhesiveness and bond durability to the dentin compared to the kits of Comparative Examples. Additionally, the dental adhesive material kits of the present invention show excellent bond durability by short-time light irradiation. Furthermore, the dental adhesive material kits show no decrease in their adhesiveness to the dentin even after the 1-year storage at 25° C., which leads to the conclusion that they have excellent storage stability too.

INDUSTRIAL APPLICABILITY

The dental adhesive material kit of the present invention is excellent in storage stability and exhibits high bond durability to a tooth structure by photopolymerization. Particularly, the dental adhesive material kit exhibits excellent adhesiveness to dentin by short-time light irradiation, and is thus suitable for abutment construction materials.

The invention claimed is:

1. A dental adhesive material kit comprising:
a dental aqueous adhesive composition (A); and
a dental curable composition (B),
wherein
the dental aqueous adhesive composition (A) comprises a (meth)acrylic polymerizable monomer (a) comprising an acid group, a vanadium compound (b), water (c), a (meth)acrylic polymerizable monomer (d) comprising an amino group, and a polymerization inhibitor (i),
the content of the polymerization inhibitor (i) is 25 to 1000 parts by weight per 100 parts by weight of the vanadium compound (b), and
the dental curable composition (B) comprises a (meth)acrylic polymerizable monomer (e) comprising no acid group, a hydroperoxide (f), a photopolymerization initiator (g), and a filler (h), does not comprise a thiourea compound, and does not comprise borate compounds.

2. The dental adhesive material kit according to claim 1, wherein the dental aqueous adhesive composition (A) comprises a (meth)acrylic polymerizable monomer (e) comprising no acid group.

3. The dental adhesive material kit according to claim 2, wherein the (meth)acrylic polymerizable monomer (e) comprising no acid group in the dental aqueous adhesive composition (A) comprises a hydrophilic (meth)acrylic polymerizable monomer (e1) comprising no acid group.

4. The dental adhesive material kit according to claim 3, wherein the hydrophilic (meth)acrylic polymerizable monomer (e1) comprising no acid group in the dental aqueous adhesive composition (A) comprises a hydrophilic (meth)acrylic polymerizable monomer comprising no monofunctional acid group.

5. The dental adhesive material kit according to claim 1, wherein the (meth)acrylic polymerizable monomer (d) comprising an amino group comprises a tertiary aminoalkyl (meth)acrylate.

6. The dental adhesive material kit according to claim 5, wherein the tertiary aminoalkyl (meth)acrylate comprises a monofunctional tertiary aminoalkyl (meth)acrylate.

7. The dental adhesive material kit according to claim 1, wherein the dental curable composition (B) does not comprise a vanadium compound (b).

8. The dental adhesive material kit according to claim 1, wherein the dental curable composition (B) comprises a polymerization accelerator (j).

9. The dental adhesive material kit according to claim 1, wherein the dental curable composition (B) is of a one-pack dental curable composition.

10. An abutment construction material kit comprising the dental adhesive material kit according to claim 1.

* * * * *